(12) United States Patent
Kimmlingen et al.

(10) Patent No.: US 9,841,475 B2
(45) Date of Patent: Dec. 12, 2017

(54) PATIENT BORE WITH INTEGRATED RADIOFREQUENCY RETURN FLUX SPACE

(71) Applicants: Ralph Kimmlingen, Zirndorf (DE); Norbert Rietsch, Dormitz (DE)

(72) Inventors: Ralph Kimmlingen, Zirndorf (DE); Norbert Rietsch, Dormitz (DE)

(73) Assignee: Siemens Aktiengesellschaft, München (DE)

( * ) Notice: Subject to any disclaimer, the term of this patent is extended or adjusted under 35 U.S.C. 154(b) by 664 days.

(21) Appl. No.: 14/306,576

(22) Filed: Jun. 17, 2014

(65) Prior Publication Data

US 2015/0015261 A1     Jan. 15, 2015

(30) Foreign Application Priority Data

Jul. 10, 2013  (DE) .................. 10 2013 213 538

(51) Int. Cl.
| | |
|---|---|
| *G01R 33/34* | (2006.01) |
| *G01R 33/36* | (2006.01) |
| *G01R 33/54* | (2006.01) |
| *G01R 33/421* | (2006.01) |
| *A61B 5/055* | (2006.01) |
| *G01R 33/3415* | (2006.01) |

(52) U.S. Cl.
CPC ... *G01R 33/3671* (2013.01); *G01R 33/34092* (2013.01); *G01R 33/421* (2013.01); *G01R 33/543* (2013.01); *A61B 5/055* (2013.01); *G01R 33/3415* (2013.01)

(58) Field of Classification Search
CPC ............ G01R 33/0011; G01R 33/0047; G01R 33/0076; G01R 33/3802; G01R 33/3854; G01R 33/3873
See application file for complete search history.

(56) References Cited

U.S. PATENT DOCUMENTS

| | | | |
|---|---|---|---|
| 4,743,853 A | 5/1988 | Frese | |
| 6,437,568 B1 | 8/2002 | Edelstein et al. | |
| 2003/0025582 A1 | 2/2003 | Arz et al. | |
| 2004/0021467 A1* | 2/2004 | Eberler | G01R 33/34007 324/318 |
| 2005/0073308 A1 | 4/2005 | Havens | |
| 2005/0127914 A1 | 6/2005 | Eberler et al. | |
| 2007/0030004 A1 | 2/2007 | Amor et al. | |

(Continued)

FOREIGN PATENT DOCUMENTS

| | | |
|---|---|---|
| CN | 1344928 A | 4/2002 |
| CN | 1399141 A | 2/2003 |

(Continued)

OTHER PUBLICATIONS

Chinese office Action for related Chinese Application No. 2014 102 08 706.7 dated Sep. 6, 2016, with English Translation.

(Continued)

*Primary Examiner* — Clayton E Laballe
*Assistant Examiner* — Ruifeng Pu
(74) *Attorney, Agent, or Firm* — Lempia Summerfield Katz LLC

(57) ABSTRACT

The embodiments relate to a magnetic resonance imaging device, where the cladding of the patient bore of the MR imaging device includes a conductive layer.

13 Claims, 3 Drawing Sheets

(56) References Cited

U.S. PATENT DOCUMENTS

| | | | |
|---|---|---|---|
| 2008/0024254 A1* | 1/2008 | Chiba | G01R 33/3804 335/216 |
| 2008/0068017 A1 | 3/2008 | Eberler et al. | |
| 2008/0169813 A1* | 7/2008 | Yamashita | G01R 33/3856 324/321 |
| 2008/0191698 A1* | 8/2008 | Nogami | G01R 33/3873 324/318 |
| 2008/0204025 A1* | 8/2008 | Eymin-Balzano | G01R 33/3873 324/320 |
| 2011/0012698 A1* | 1/2011 | Hutton | G01R 33/3802 335/216 |
| 2012/0098538 A1* | 4/2012 | Shen | G01R 33/3873 324/318 |
| 2013/0237805 A1* | 9/2013 | Dietz | G01R 33/3854 600/410 |
| 2013/0278262 A1* | 10/2013 | Zhai | G01R 33/34 324/309 |
| 2014/0061202 A1* | 3/2014 | Mathieu | G01R 33/3804 220/560.09 |
| 2014/0274721 A1* | 9/2014 | Calvert | G01R 33/3815 505/162 |
| 2015/0097566 A1* | 4/2015 | Grodzki | G01R 33/288 324/322 |
| 2015/0145516 A1* | 5/2015 | Ueda | G01R 33/3854 324/322 |

FOREIGN PATENT DOCUMENTS

| | | |
|---|---|---|
| CN | 1534305 A | 10/2004 |
| CN | 1611186 A | 5/2005 |
| CN | 1798981 A | 7/2006 |
| CN | 101120876 A | 2/2008 |
| DE | 4301567 A1 | 8/1993 |
| DE | 18938390 A1 | 3/2000 |
| DE | 10314215 B4 | 11/2006 |
| DE | 102008047814 A1 | 4/2010 |
| JP | 2098003 A | 4/1990 |
| JP | H05344983 A | 12/1993 |

OTHER PUBLICATIONS

German Search Report dated Dec. 6, 2013 for corresponding DE 102013213538.6.

German Office action for related German Application No. 10 2013 213 538.6, dated Dec. 1, 2015, with English Translation.

* cited by examiner

PATENT BORE WITH INTEGRATED RADIOFREQUENCY RETURN FLUX SPACE

CROSS-REFERENCE TO RELATED APPLICATIONS

This application claims the benefit of DE 10 2013 213538.6, filed on Jul. 10, 2013, which is hereby incorporated by reference in its entirety.

TECHNICAL FIELD

The embodiments relate to a magnetic resonance imaging device.

BACKGROUND

Magnetic resonance devices (MRIs) for examining objects or patients are known from DE 103 14 215 B4, for example.

SUMMARY

It is an object of the present embodiments to optimize further a magnetic resonance imaging device.

The scope of the present invention is defined solely by the appended claims and is not affected to any degree by the statements within this summary. The present embodiments may obviate one or more of the drawbacks or limitations in the related art.

DETAILED DESCRIPTION

Figure 3:
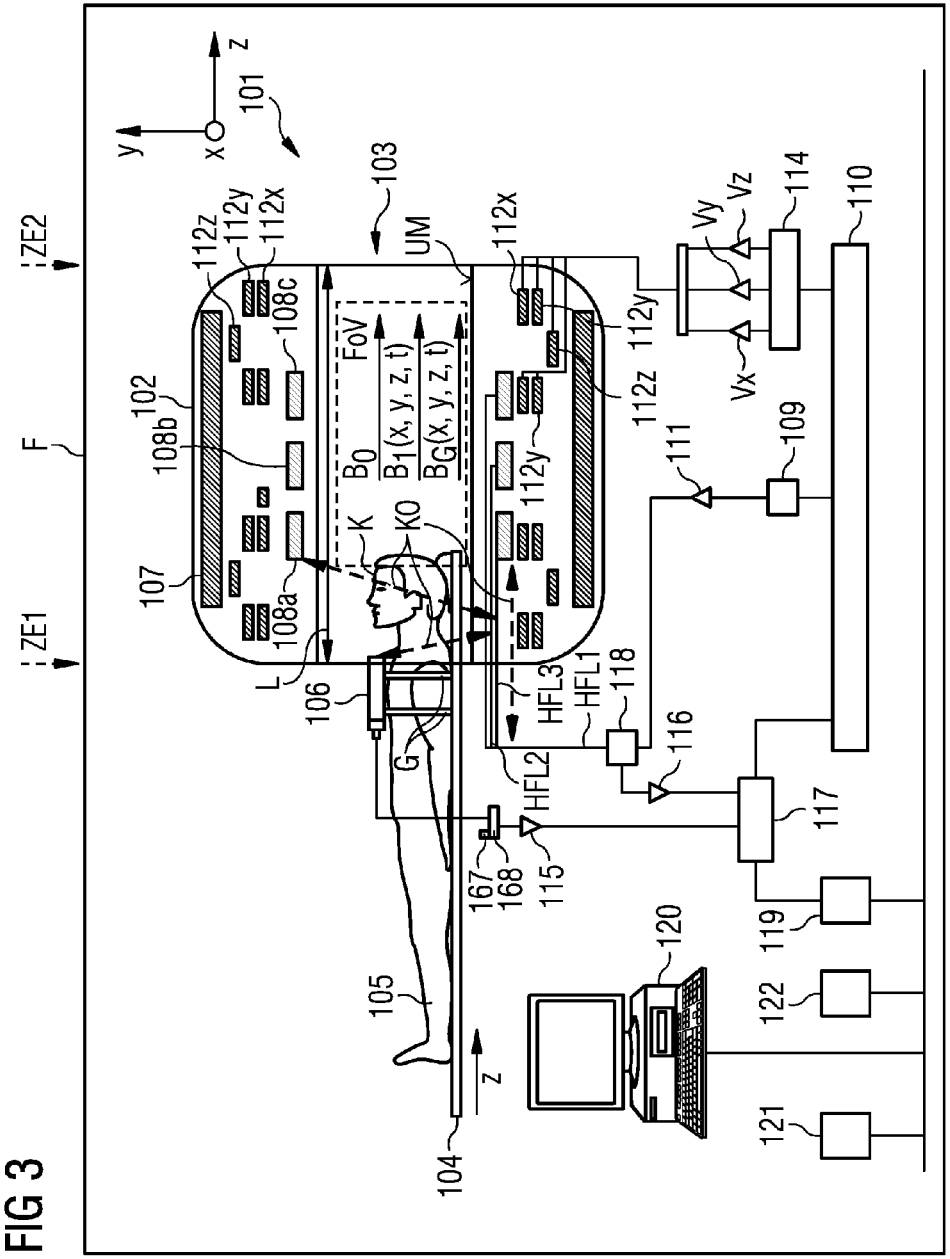
FIG. 3 schematically depicts an embodiment of a MRI system.

FIG. 3 depicts a magnetic resonance imaging MRI device 101 (situated in a shielded room or in a Faraday cage F) with a whole body coil 102 with a space 103 (also referred to as bore or patient bore). The space or patient bore 103 is tubular in this case, in which a patient couch 104 with a body of, for example, an examination object or patient 105, with or without local coil arrangement 106, may be driven in the direction of the arrow z in order to generate recordings of the patient 105 by an imaging method. Arranged on the patient in this case is a local coil arrangement 106, by which it is possible, in a local region (also referred to as field of view or FOV) of the MRI device, to generate recordings of a portion of the body 105 in the FOV. Signals of the local coil arrangement 106 may be evaluated (e.g., converted into images, stored, or displayed) by an evaluation apparatus (168, 115, 117, 119, 120, 121, etc.) of the MRI device 101. The MRI device 101 may be connected to the local coil arrangement 106 by, for example, coaxial cables or a radio 167, etc.

In order to use a magnetic resonance imaging MRI device 101 to examine a body 105 (an examination object or a patient) by magnetic resonance imaging, different magnetic fields are radiated onto the body 105, which magnetic fields are matched very precisely to one another in terms of their temporal and spatial characteristics. A strong magnet or main-field magnet 107 (e.g., a cryo-magnet) in a measuring cabin with an opening 103 (e.g., a tunnel-shaped opening) generates a static strong main magnetic field $B_0$. The magnetic field may be 0.2 tesla (T) to 3 tesla (T) or more. A body 105 to be examined, arranged on a patient couch 104, is driven into a region of the main magnetic field $B_0$ that is approximately homogeneous in the observation region FOV ("field of view"). The nuclear spins of atomic nuclei of the body 105 are excited by magnetic radiofrequency excitation pulses $B_1$ (x, y, z, t), which may be radiated by a radiofrequency antenna that is depicted as a body coil 108 (e.g., multi-part=108a, 108b, 108c) and/or a local coil arrangement. Radiofrequency excitation pulses may be generated by a pulse generation unit 109 that is controlled by a pulse sequence control unit 110. After amplification by a radiofrequency amplifier 111, the pulses are routed to the radiofrequency antenna 108. In certain embodiments, more than one pulse generation unit 109, more than one radiofrequency amplifier 111, and/or several radiofrequency antennas 108a, b, c may be employed in a magnetic resonance imaging device 101.

Furthermore, the magnetic resonance imaging device 101 includes gradient coils 112x, 112y, 112z, by which magnetic gradient fields $B_G$ (x, y, z, t) for selective layer excitation and for spatial encoding of the measurement signal are radiated in during a measurement. The gradient coils 112x, 112y, 112z are controlled by a gradient coil control unit 114 (and optionally via amplifiers Vx, Vy, Vz), which, like the pulse generation unit 109, is connected to the pulse sequence control unit 110.

Signals emitted by the excited nuclear spins of the atomic nuclei in the examination object are received by the body coil 108 and/or at least one local coil arrangement 106, amplified by associated radiofrequency preamplifiers 116 and processed further and digitized by a reception unit 117. The recorded measurement data are digitized and stored as complex number values in a k-space matrix. An associated MR image may be reconstructed from the k-space matrix filled with values by means of a multidimensional Fourier transform.

For a coil that may be operated both in the transmission and in the reception mode, such as, for example, the body coil 108 or a local coil 106, the correct signal transmission is regulated by an upstream transmission/reception switch 118. An image processing unit 119 generates an image from the measurement data. The image is displayed to a user via an operating console 120 and/or stored in a storage unit 121. A central computer unit 122 controls the individual components of the installation.

In MR imaging, images with a high signal-to-noise ratio (SNR) may be recorded using local coil arrangements (herein, coils or local coils). The local coil arrangements are antenna systems that are attached in the direct vicinity on (anterior), under (posterior), at the body 105, or in the body 105. During a MR measurement, the excited nuclei induce a voltage in the individual antennas of the local coil, which voltage is then amplified using a low-noise preamplifier (e.g., LNA, preamp), and relayed to the reception electronics. In order to improve the signal-to-noise ratio, even in the case of high-resolution images, use is made of so-called high-field installations (e.g., 1.5 T-12 T or more). If it is possible to connect more individual antennas to a MR reception system than there are receivers available, a switching matrix (also referred to as RCCS) may be installed between reception antennas and receiver. The switching matrix routes the currently active reception channels (e.g., those that currently lie in the field of view of the magnet) to the available receivers. As a result of the switching matrix, it is possible to connect more coil elements than there are receivers available since, in the case of whole body coverage, only those coils situated in the FOV (field of view) or in the homogeneity volume of the magnet may be read out.

By way of example, an antenna system that may include one antenna element, or as array coil of several antenna elements (e.g., coil elements) may be referred to as a local coil arrangement 106. These individual antenna elements may be configured as loop antennas (loops), butterfly coils, flex coils, or saddle coils. By way of example, a local coil arrangement includes coil elements, a preamplifier, further electronics (sheath current chokes, etc.), a housing, supports, and/or a cable with plugs that are connected to the MRI device. A receiver 168, attached on the installation side, filters and digitizes a signal received from a local coil 106 (e.g., by radio, etc.), and transmits the data to a digital signal processing apparatus. The digital signal processing apparatus may derive an image or spectrum from the data obtained by a measurement and make the image available to the user for a subsequent diagnosis by him and/or for storage purposes, for example.

Figure 1:
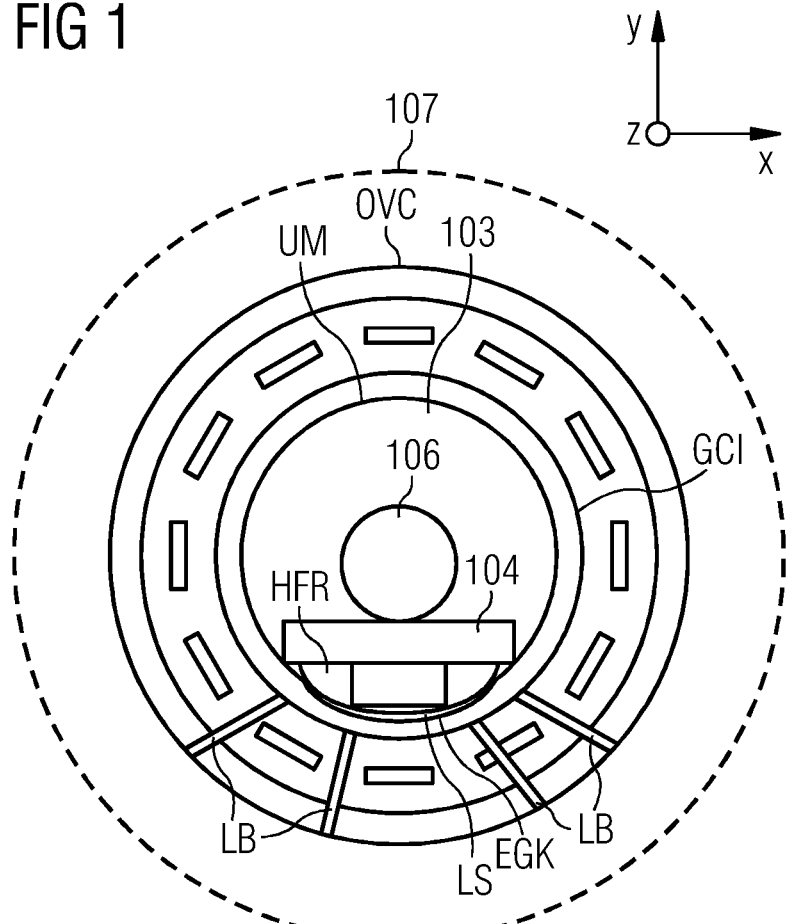
FIG. 1 depicts an embodiment of a MRI system with a radiofrequency (RF) return flux space optimized by a conductive layer.
Figure 2:
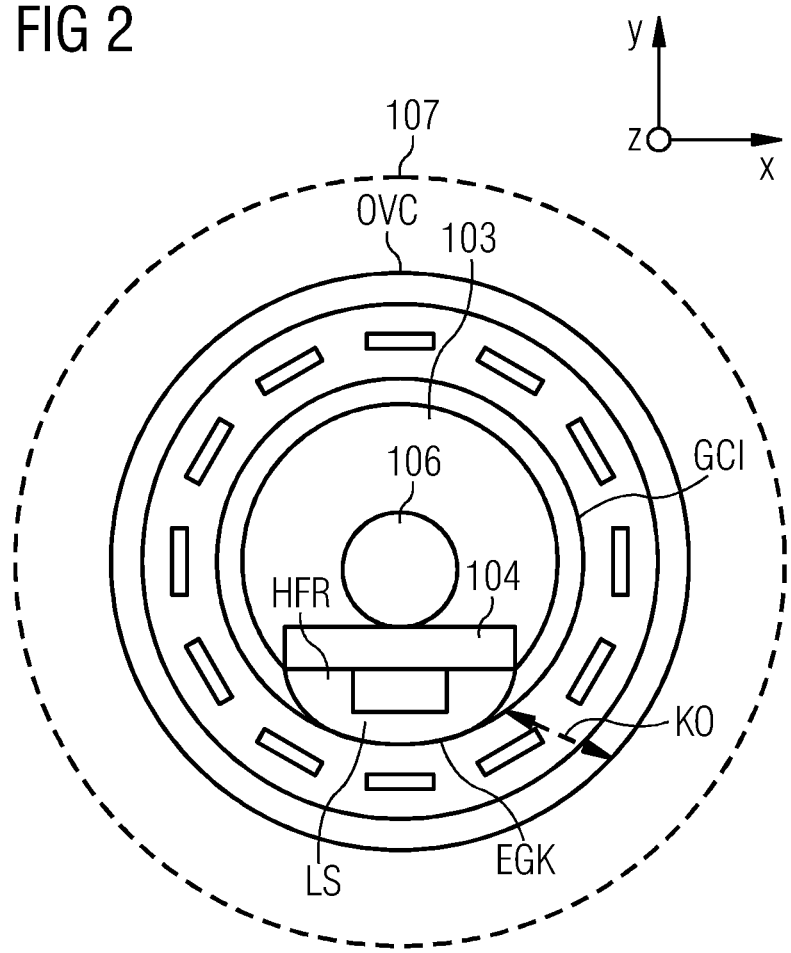
FIG. 2 depicts an embodiment of a MRI system with a RF return flux space.

FIG. 1 depicts a MRI 101 with a RF return flux space HFR, which is reduced compared to the MRI 101 depicted in FIG. 2 as a result of a conductive layer LS. The return flux space (HFR) therefore, for example, does not extend, or only extends to a lesser extent than in FIG. 2, into the region GCI of the gradient coils of the MRI and/or does not extend, or only extends to a lesser extent, into the region of the local coil 106. The return flux space may optionally, in an improved manner, decouple gradient coils and/or a local coil (in an improved manner) from radiofrequency transmission and reception lines (energy chain) of the patient bore 103.

Radiofrequency (RF) transmission and reception lines, such as, for example, HFL1, HFL2, HFL3, etc. in FIG. 3 (also referred to here as part of an energy chain), on the patient bore 103 of a MRI system 101 may couple inductively and capacitively with the RF transmission coils (such as, e.g., 108a-c, 106) of the MRI 101.

This coupling (indicated by the arrows KO) depends on the location of the transmission structures 108a-c, 106 and of the lines HFL1, HFL2, HFL3, etc., relative to the ground plane OVC in the form of, for example, the inner bore (also referred to as OVC) (e.g. an inner side of the main-field magnet 107 facing the patient). A significant power influx in the lines HFL1, HFL2, HFL3 causes the existence of a return flux space HFR of the standing RF wave between energy chain EGK and ground plane such as, for example, OVC. If these circumstances apply, part of the transmission energy in the case of transmission by the MRI 101 may be transferred to the lines in the energy chain. As a result, overheating of the energy chain with potential material damage is feasible. Interference of the transmission field by the waves returning as far as to the transmission coil is also feasible.

In 1.5 T and 3 T systems, the energy chain EGK in the patient couch 104 may be surrounded by a sheath wave choke (MWS). The latter is tuned to the respective MR frequency (60 or 125 MHz) and damps the coupled-in waves by approximately 30 decibels (dB). The remaining amplitude is small enough so as not to cause significant interference.

In high-field systems (>7 T), it may be expedient to manufacture an individual sheath wave choke MWS for each field strength. Previously, the approach of an energy chain EGK situated on the maintenance side in the patient bore 103 was selected. Due to the short wavelength at >7 T, no volume transmission coils (body coils) (conventional at 1.5 and 3 T) are, at least in internally known MRIs of this type, used to date, and so there may be almost no coupling-in using this strategy. A disadvantage of this solution may include the fact that a vertical movement of the couch would not be possible. Therefore, a solution may be a U-shaped guidance of the energy chain under the couch to the side of the patient. In the process, the radial distance of the energy chain from the OVC is approximately 20 mm. Hence, the return flux space for the coupling-in waves is small, but a residual risk remains. An advantage of this solution is that a vertical movement of the couch is possible.

According to one embodiment, a (highly) conductive layer LS is introduced (e.g., a slotted copper structure, a copper fabric, or a different conductor made of metal) into the molded body (e.g., the cladding UM) (e.g., formed by resin, etc., by casting or winding) of the patient bore 103 (e.g., glass-fiber reinforced plastic (GRP) tube) in the region of the energy chain EGK. This conductive layer LS is connected to the OVC (system ground point or system-ground-point) at a plurality of points (e.g., at the cylinder ends). The connection may be by solder strips LB. As a result, it is possible to reduce the return flux space HFR and therefore reduce the energy that may potentially be coupled-in to a minimum. The small distance to the ground plane OVC is unproblematic due to an insulation of the cables in the energy chain EGK.

The conductive layer LS may have any thickness.

In accordance with one embodiment, a patient bore 103 with integrated RF return flux space shaping is described for minimizing the coupling between an energy chain EGK and local RF transmission coils 106.

Advantages of the patient bore embodiments may include: (a) sheath wave chokes may be dispensed with, (b) the patient bore may work independently of frequency, (c) the patient bore may result in coupling-in being avoided rather than the coupled-in power being dissipated, and/or (d) the patient bore may be simple and cost-effective in comparison to conventional technology.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance imaging device comprising:
   a patient couch;
   a body coil arrangement;
   a local coil arrangement; and
   a patient bore having cladding positioned between the body coil arrangement and the patient couch,
      wherein the cladding comprises a conductive layer
         arranged in a region of an energy chain of the patient bore below a surface of the patient couch configured to support a patient, wherein a width of the conductive layer is less than a width of the patient couch as measured in direction parallel with the surface of the patient couch, wherein the energy chain comprises radiofrequency transmission and reception lines, and wherein the conductive layer is configured to reduce a return flux space or an energy coupled into the local coil arrangement.

2. The magnetic resonance imaging device as claimed in claim 1, wherein the conductive layer is arranged in, or on, the cladding, and wherein the cladding surrounds the patient bore in a longitudinal direction, the cladding surrounds a circumference of the patient bore, or the cladding surrounds the patient bore in the longitudinal direction and the cladding surrounds the circumference of the patient bore.

3. The magnetic resonance imaging device as claimed in claim 1, wherein the conductive layer extends along a longitudinal direction of the patient bore.

4. The magnetic resonance imaging device as claimed in claim 3, wherein the conductive layer extends along more than 50% of a length of the patient bore in the longitudinal direction.

5. The magnetic resonance imaging device as claimed in claim 4, wherein the conductive layer is connected in an electrically conductive manner to a system ground point of the magnetic resonance imaging device at a plurality of points.

6. The magnetic resonance imaging device as claimed in claim 1, wherein the conductive layer is arranged in the molded body or glass-fiber reinforced plastic tube of the patient bore.

7. The magnetic resonance imaging device as claimed in claim 1, wherein the conductive layer comprises a metal.

8. The magnetic resonance imaging device as claimed in claim 7, wherein the metal is copper.

9. The magnetic resonance imaging device as claimed in claim 1, wherein the conductive layer comprises a slotted copper structure or a copper fabric.

10. The magnetic resonance imaging device as claimed in claim 1, wherein the conductive layer is connected in an electrically conductive manner to a system ground point of the magnetic resonance imaging device at a plurality of points.

11. The magnetic resonance imaging device as claimed in claim 10, wherein the conductive layer is connected to the system ground point at the plurality of points by solder strips, each solder strip extending in a radial direction between the conducive layer and the system ground point.

12. The magnetic resonance imaging device as claimed in claim 10, wherein the plurality of points is located at the cylinder ends of the patient bore.

13. The magnetic resonance imaging device as claimed in claim 1, wherein the conductive layer or cables have an electrical insulation for connecting the conductive layer to a ground plane of an inner bore of a main-field magnet of the magnetic resonance imaging device.

* * * * *